United States Patent
Farmer et al.

(10) Patent No.: US 7,507,402 B1
(45) Date of Patent: Mar. 24, 2009

(54) **TOPICAL USE OF PROBIOTIC *BACILLUS* SPORES TO PREVENT OR CONTROL MICROBIAL INFECTIONS**

(75) Inventors: Sean Farmer, San Diego, CA (US); Robert J. Mikhail, Lakeside, CA (US)

(73) Assignee: Ganeden Biotech, Inc., Mayfield Heights, OH (US)

( * ) Notice: Subject to any disclaimer, the term of this patent is extended or adjusted under 35 U.S.C. 154(b) by 0 days.

(21) Appl. No.: 09/509,159

(22) PCT Filed: Apr. 10, 1998

(86) PCT No.: PCT/US98/07307

§ 371 (c)(1), (2), (4) Date: May 28, 2003

(87) PCT Pub. No.: WO98/47374

PCT Pub. Date: Oct. 29, 1998

(51) Int. Cl.
*A01N 63/00* (2006.01)
*C12N 1/20* (2006.01)

(52) U.S. Cl. .................. 424/94.46; 424/93.4; 435/832; 435/252.31

(58) Field of Classification Search ............... 424/93.46
See application file for complete search history.

(56) References Cited

U.S. PATENT DOCUMENTS

| | | | | |
|---|---|---|---|---|
| 4,110,477 A | | 8/1978 | Naruse et al. ............... 426/46 |
| 4,871,539 A | | 10/1989 | Hata et al. .................. 424/93 |
| 5,000,939 A | * | 3/1991 | Dring et al. ................. 424/48 |
| 5,045,314 A | * | 9/1991 | Bone et al. ................. 424/93.46 |
| 5,176,911 A | | 1/1993 | Tosi et al. ................... 424/83 J |
| 5,344,647 A | | 9/1994 | Rossall ..................... 424/93.462 |
| 5,431,924 A | | 7/1995 | Ghosh et al. ................. 424/522 |
| 5,455,028 A | | 10/1995 | O'Donnell ............... 424/93.46 |
| 6,461,607 B1 | * | 10/2002 | Farmer ..................... 424/93.45 |

FOREIGN PATENT DOCUMENTS

| | | |
|---|---|---|
| GB | 1 204 017 | 9/1970 |
| JP | 63-96107 | 4/1988 |
| JP | 3-192200 | * 8/1991 |
| WO | WO 93/14187 | 7/1993 |

OTHER PUBLICATIONS

Seligman S.A. "Doderlein's bacilli: friend or foe?" British Journal of Obstetrics and Gynaecology. Oct. 1995, vol. 102, pp. 763-764.*
Gibson et al. Gastroenterology. 1995. 108: p. 975.*
O'Sullivan et al. "Probiotic bacteria: myth or reality?". Trends in Food Science and Technology. 1992. 31:309-314.*
Fuller R. "Probiotics in man and animals". Journal of Applied Bacteriology. 1989, 66: 365-378.*
Database Medline, Moldenhauer, et al., Abstract only, Database accession No. NLM7489197, Sep. 1995.
Database WPI, Abstract only, Section Ch, Week 199309, Derwent Publications Ltd., London, GB, AN 1993-073946.
Database WPI, Abstract only, Section Ch, Week 199734, Derwent Publications Ltd., London, GB, AN 1997-367033.
Database WPI, Abstract only, Section Ch, Week 199637, Derwent Publications Ltd., London, GB, AN 1996-368043.
Gorbach, S.L., *Ann Med.*, 22(1):37-41 (1990).
Klaenhammer, T.R., *FEMS Microbiol. Rev.*, 12(1-3):39-85 (1993).
Reid, et al., *Clin. Microbiol. Rev.*, 3(4):335-344 (1990).
Schoeni, et al., *Applied Environ. Microbiol.*, 60(4):1191-1197 (1994).
Siegel, et al., *J. Econ. Entomol.*, 83(2):347-355 (1990).
Sytnik, S.I., *Mikrobiologicheskii Zhurnal*, 51(1):82-87 (1989).
Mohan et al., "Short term hypolipidemic effects of oral *Lactobacillus sporogenes* therapy in patients with primary dyslipidemias", *Indian Heart Journal*, 42(5):361-364 (1990).

* cited by examiner

*Primary Examiner*—Vera Afremova
(74) *Attorney, Agent, or Firm*—Ingrid A. Beattie; Mintz, Levin, Cohn, Ferris, Glovsky and Popeo, P.C.

(57) ABSTRACT

Compositions including an isolated *Bacillus* species, spores or an extracellular product of *B. coagulans*, suitable for topical application, for inhibiting growth of yeast, fungus, bacteria or Herpes simplex virus are disclosed. Methods of inhibiting growth of yeast, fungus, bacteria or Herpes simplex virus by topical application of compositions that include an isolated *Bacillus* species, spores or an extracellular product of a *B. coagulans* strain are disclosed.

38 Claims, No Drawings

TOPICAL USE OF PROBIOTIC *BACILLUS* SPORES TO PREVENT OR CONTROL MICROBIAL INFECTIONS

TECHNICAL FIELD

This invention relates to utilizing a probiotic *Bacillus* organism in a therapeutic composition as a topical agent, and specifically relates to the use of compositions derived from *Bacillus coagulans* for prevention and control of microbial infections.

BACKGROUND OF THE INVENTION

Probiotic agents are organisms that confer a benefit when they grow in a particular environment, often by inhibiting the growth of other biological organisms in the same environment. Examples of probiotics include bacteria and bacteriophages which can grow in the intestine, at least temporarily, to displace or destroy pathogens and provide other benefits to the host organism (Salminen et al, *Antonie Van Leeuwenhoek,* 70 (2-4): 347-358, 1996; Elmer et al, *JAMA,* 275:870-876, 1996; Rafter, *Scand. J. Gastroenterol.* 30:497-502, 1995; Perdigon et al, *J. Dairy Sci.* 78:1597-1606, 1995; Gandi, *Townsend Lett. Doctors & Patients,* pp. 108-110, January 1994; Lidbeck et al, *Eur. J. Cancer Prev.* 1:341-353, 1992). Probiotic preparations were systematically evaluated for their effect on health and longevity in the early 1900's (Metchnikoff, E., *Prolongation of Life,* Wilham Heinemann, London, 1910; republished by G. P. Putnam's Sons, New York, N.Y., 1970). Since the discovery and widespread use of antibiotics in about 1950 to treat pathological microbes, the use of probiotics has been limited.

The widespread use of antimicrobial drugs, especially broad spectrum antibiotics, has produced serious consequences. Individuals taking antibiotics often suffer from gastrointestinal upset when beneficial microorganisms in the gut are killed, thus changing the balance of the intestinal flora. This imbalance can result in vitamin deficiencies when vitamin-producing gut bacteria are killed and/or illness when a pathogenic organism overgrows and replaces the beneficial gut microorganisms. In addition to gut microflora, beneficial and/or pathological microorganisms can inhabit the oral cavity, the genital area and the vagina (Thomason J. L. et al., *Am. J. Obstet. GynecoL* 165 (4 Pt. 2):1210-1217, 1991; Marsh, P. D., *Caries Res.* 27 (Suppl. 1):72-76, 1993; Lehner T., *Vaccine* 3(1): 65-68, 1985; Hill L. V. & Embil, J. A., *Can. Med. Assoc. J.* 134(4):321-331, 1986). The use of antimicrobial drugs can similarly cause an imbalance in those microorganisms and the therapeutic use of probiotic bacteria, especially *Lactobacillus* strains, that colonize those areas has been disclosed (Winberg, J. et al., *Pediatr. Nephrol.* 7(5):509-514, 1993; Malin M. et al., *Ann. Nutr. Metab.* 40(3); 137-145, 1996; U.S. Pat. No. 5,176,911).

Increasing numbers of pathogenic microorganisms have developed antibiotic resistance, requiring the development and use of second and third generation antibiotics. Microorganisms that are resistant to multiple drugs have also developed, often with multiple drug resistance spreading between species, leading to serious infections that cannot be controlled by use of antibiotics.

Opportunistic microbial infections often occur in immunodeficient individuals. Immunodeficient individuals have impaired natural immunity allowing pathogenic microorganisms to survive and grow, either internally or externally, due to the individual's diminished immune response to the pathogen. Immunodeficiency can result from genetic conditions, diseases such as AIDS, or therapeutic treatments such as cancer therapy (chemotherapy or radiation treatment) and drug-mediated immunosuppression following organ transplant. Inhibition of pathogenic microorganisms by probiotics is useful for preventing or treating opportunistic infections, particularly in immunodeficient individuals.

Thus, there is a need for preventive and therapeutic agents that can control the growth of pathogenic microorganisms without the use of antibiotic chemicals to which the microorganisms already are or can become resistant. Probiotics can be applied either internally or externally to restore the balance of beneficial microorganisms to pathogens, without contributing to the evolution of drug-resistant pathogens.

Lactic acid producing bacteria (e.g., *Bacillus, Lactobacillus* and *Streptococcus* species) have been used as food additives and there have been some claims that they provide nutritional and therapeutic value (Gorbach S. L., *Ann. Med.* 22(1):37-41, 1990; Reid, G. et al., *Clin. Microbiol. Rev.* 3(4): 335-344, 1990). Some lactic acid producing bacteria (e.g., those used to make yogurt) have been suggested to have antimutagenic and anticarcinogenic properties useful for preventing human tumors (Pool-Zobel B. L. et al., *Nutr. Cancer* 20(3):261-270, 1993; U.S. Pat. No. 4,347,240). Some lactic acid producing bacteria also produce bacteriocins which are inhibitory metabolites responsible for the bacteria's antimicrobial effects (Klaenhammer T. R., *FEMS Microbiol Rev.* 12(1-3):39-85, 1993; Barefoot S. F. & Nettles C. G., *J. Dairy Sci.* 76(8):2366-2379, 1993).

Selected *Lactobacillus* strains that produce antibiotics have been disclosed as effective for treatment of infections, sinusitis, hemorrhoids, dental inflammations, and other inflammatory conditions (U.S. Pat. No. 4,314,995). *L. reuteri* produces antibiotics with activity against Gram negative and Gram positive bacteria, yeast and a protozoan (U.S. Pat. No. 5,413,960 and U.S. Pat. No. 5,439,678). *L. casei* ssp. *rhamnosus* strain LC-705, DSM 7061, alone or in combination with a *Propionibacterium* species, in a fermentation broth has been shown to inhibit yeast and molds in food and silage (U.S. Pat. No. 5,378,458). Also, antifungal *Serratia* species have been added to animal forage and/or silage to preserve the animal feedstuffs, particularly *S. rubidaea* FB299, alone or combined with an antifungal *B. subtilis* (strain FB260) (U.S. Pat. No. 5,371,011).

*Bacillus coagulans* is a non-pathogenic gram positive spore-forming bacteria that produces L(+) lactic acid (dextrorotatory) in homofermentation conditions. It has been isolated from natural sources, such as heat-treated soil samples inoculated into nutrient medium (*Bergey's Manual of Systemic Bacteriology*, Vol. 2, Sneath, P. H. A. et al., eds., Williams & Wilkins, Baltimore, Md., 1986). Purified *B. coagulans* strains have served as a source of enzymes including endonucleases (e.g., U.S. Pat. No. 5,200,336), amylase (U.S. Pat. No. 4,980,180), lactase (U.S. Pat. No. 4,323,651) and cyclo-malto-dextrin glucano-transferase (U.S. Pat. No. 5,102,800). *B. coagulans* has been used to produce lactic acid (U.S. Pat. No. 5,079,164). A strain of *B. coagulans* (referred to as *L. sporogenes* Sakaguti & Nakayama (ATCC 31284)) has been combined with other lactic acid producing bacteria and *B. natto* to produce a fermented food product from steamed soybeans (U.S. Pat. No. 4,110,477). *B. coagulans* strains have also been used as animal feed additives for poultry and livestock to reduce disease and improve feed utilization and, therefore, to increase growth rate in the animals (International PCT Pat. Applications No. WO 9314187 and No. WO 9411492).

SUMMARY OF THE INVENTION

It has now been discovered that *Bacillus* species possess the ability to exhibit probiotic activity in aerobic conditions such as on skin or mucous membrane tissues and thereby treat, control and/or inhibit numerous conditions caused by microbial infections.

The invention describes therapeutic compositions, articles of manufacture and methods of use for inhibiting various microbial infections caused by bacteria, yeast, fungus or virus, which utilize isolated *Bacillus* species.

There are several *Bacillus* species useful according to the present invention, including *Bacillus coagulans, Bacillus subtilis, Bacillus laterosporus* and *Bacillus* laevolacticus. Although exemplary of the invention, *Bacillus coagulans* is only a model for the other *Bacillus* species, and therefore the invention is not to be considered as limiting.

According to the invention, there is provided a composition comprising an isolated *Bacillus* species in a pharmaceutically acceptable carrier suitable for topical application to skin or a mucous membrane of a mammal. In one embodiment of the composition, the *Bacillus* species is included in the composition in the form of spores. In another embodiment, the *Bacillus* species is included in the composition in the form of a dried cell mass. In the composition, the carrier may be an emulsion, cream, lotion, gel, oil, ointment, suspension, aerosol spray, powder, aerosol powder or semi-solid formulation.

According to a preferred aspect of the invention, there is provided a composition comprising an extracellular product of a *Bacillus coagulans* species in a pharmaceutically acceptable carrier suitable for topical application to skin or a mucous membrane of a mammal. In one embodiment, the extracellular product is a supernatant or filtrate of a culture of an isolated *Bacillus coagulans* species. The carrier may be an emulsion, cream, lotion, gel, oil, ointment, suspension, aerosol spray, powder, aerosol powder or semi-solid formulation.

According to another aspect of the invention, there is provided a method of preventing bacterial, yeast, fungal or viral infection including the steps of applying topically to skin or a mucous membrane of a mammal a probiotic composition comprising an isolated *Bacillus* species; and allowing the *Bacillus* species to grow topically for sufficient time to inhibit growth of bacteria, yeast, fungus or virus. One embodiment further includes the steps of providing spores of the *Bacillus* species in the probiotic composition, and allowing the spores to germinate after the applying step. In one embodiment, the step of allowing the *Bacillus* species to grow inhibits growth of one or more microbe species selected from the group consisting of *Staphylococcus* species, *Streptococcus* species, *Pseudomonas* species, *Escherichia coli, Gardnerella vaginalis, Propionibacterium acnes, Aeromonas hydrophilia, Aspergillus* species, *Proteus* species, *Aeromonas* species, *Clostridium* species, *Klebsiella* species, *Candida* species and *Trichophyton* species. Also inhibited are certain virus species. In another embodiment, the applying step is applying a probiotic composition in the form of a cream, lotion, gel, oil, ointment, suspension, aerosol spray, powder, aerosol powder or semi-solid formulation.

According to another aspect of the invention, there is provided a method of inhibiting growth of bacteria, yeast, fungus, virus or a combination thereof, including the steps of applying topically to skin or a mucous membrane a composition comprising an extracellular product of an isolated *Bacillus coagulans* species, and allowing the composition to be present for sufficient time to inhibit growth of bacteria, yeast, fungus, virus or any combination thereof. In one embodiment, the applying step includes applying the composition in the form of a cream, lotion, gel, oil, ointment, suspension, aerosol spray, powder, aerosol powder or semi-solid formulation.

According to another aspect of the invention, there is provided a composition comprising an isolated *Bacillus* species applied to a flexible article that is intended to be worn by or attached to skin or a mucous membrane of a mammal to allow probiotic activity of the isolated *Bacillus* species to occur adjacent to or on the skin or mucous membrane.

According to another aspect of the invention, there is provided a method of inhibiting growth of bacteria, yeast, fungus, virus or any combination thereof, including the steps of applying a composition comprising an isolated *Bacillus* species to a solid surface, contacting the solid surface with the applied *Bacillus* species thereon to skin or a mucous membrane of a mammal, and allowing the solid surface to contact the skin or mucous membrane for sufficient time to allow initiation of probiotic activity of the isolated *Bacillus* species to inhibit growth of bacteria, yeast, fungus, virus or a combination thereof adjacent to or on the skin or mucous membrane. In one embodiment, the applying step includes applying the composition to a diaper, pliable material for wiping skin or a mucous membrane, dermal patch, adhesive tape, absorbent pad, tampon or article of clothing. In another embodiment, the applying step includes impregnating the composition into a fibrous or nonfibrous solid matrix.

The invention also describes a therapeutic system for treating, reducing or controlling microbial infections comprising a container comprising a label and a therapeutic composition as described herein, wherein said label comprises instructions for use of the composition for treating infection.

The invention provides several advantages. In particular, insofar as there is a detrimental effect to the use of antibiotics because of the potential to produce antibiotic-resistant microbial species, it is desirable to have an antimicrobial therapy which does not utilize conventional antimicrobial reagents. The present invention does not contribute to the production of future generation of antibiotic resistant pathogens.

It should be understood that both the foregoing general description and the following detailed description are exemplary and explanatory only and are not restrictive of the invention as claimed.

DETAILED DESCRIPTION OF THE INVENTION

The present invention is directed to the discovery that *Bacillus* species can be used in therapeutic compositions as a probiotic for preventing or controlling microbial infections. As discussed further, the compositions can be formulated in many configurations because the bacterium is presented as a viable organism, either as a vegetative cell or as a spore, and colonizes the tissue of interest. The cells/spores can be presented in compositions suited for topical application to a tissue, or in suspensions such as a bath, or on flexible materials such as diapers, bandaids, tampons and the like personal articles, all directed at the objective of introducing the bacteria topically to skin or a mucous membrane tissue.

A *Bacillus* species can be a species selected from the group of *Bacillus coagulans, Bacillus subtilis, Bacillus laterosporus* and *Bacillus laevolacticus*, all of which have the ability to form spores, and can colonize tissue aerobically. Thus, although many of the examples herein refer to the *Bacillus coagulans* species in particular, it is intended that any of the *Bacillus* species can be used in the compositions, articles of manufacture, systems and method of the present invention.

A *Bacillus* species is particularly suited for the present invention due to the properties in common between species of the *Bacillus* genus, including in particular the ability to form spores which are relatively resistant to heat and other conditions, making them ideal for storage (shelf-life) in product formulations, and ideal for survival and colonization of tissues under conditions of pH, salinity, and the like on tissues subjected to microbial infection. Additional useful properties include non-pathogenic, aerobic, facultative and heterotrophic, rendering these species safe, and able to colonize skin and mucous membrane tissues.

There are a variety of different *Bacillus* species, including, but not limited to many different strains available through commercial and public sources, such as the American Tissue Culture Collection (ATCC). For example, *Bacillus coagulans* strains are available as ATCC Accession Numbers 15949, 8038, 35670, 11369, 23498, 51232, 11014, 31284, 12245, 10545 and 7050. *Bacillus subtilis* strains are available as ATCC Accession Numbers 10783, 15818, 15819, 27505, 13542, 15575, 33234, 9943, 6051a, 25369, 11838, 15811, 27370, 7003, 15563, 4944, 27689, 43223, 55033, 49822, 15561, 15562, 49760, 13933, 29056, 6537, 21359, 21360, 7067, 21394, 15244, 7060, 14593, 9799, 31002, 31003, 31004, 7480, 9858, 13407, 21554, 21555, 27328 and 31524. *Bacillus laterosporus* strains are available as ATCC Accession Numbers 6456, 6457, 29653, 9141, 533694, 31932 and 64, including *Bacillus laterosporus BOD*. *Bacillus laevolacticus* strains are available as ATCC Accession Numbers 23495, 23493, 23494, 23549 and 23492.

The growth of these various *Bacillus* species to form cell cultures, cell pastes and spore preparations is generally well known in the art. Exemplary culture and preparative methods are described herein for *Bacillus coagulans* and can readily be used for the other *Bacillus* species.

Exemplary methods and compositions are described herein using *Bacillus coagulans* as a probiotic for controlling, treating or reducing microbial infections.

As used herein, "probiotic" refers to microorganisms (e.g., bacteria, yeast, viruses and/or fungi) that form at least a part of the transient or endogenous flora and, thus, have a beneficial prophylactic and/or therapeutic effect on the host organism. Probiotics are generally known to be safe by those skilled in the art. Although not wishing to be bound by any particular mechanism, the probiotic activity of *Bacillus* species is thought to result from competitive inhibition of growth of pathogens due to superior colonization, parasitism of undesirable microorganisms, lactic acid production and/or other extracellular products having antimicrobial activity, or combinations thereof. These products and activities of *Bacillus* may act synergistically to produce the beneficial probiotic effect.

A. *Bacillus coagulans* Compositions

We have demonstrated that purified *Bacillus coagulans* is exemplary and preferred as a probiotic for biological control of various microbial pathogens.

Because *B. coagulans* forms heat-resistant spores, it is particularly useful for making pharmaceutical compositions for treating microbial infections. Topical formulations that include viable *B. coagulans* spores in a pharmaceutically acceptable carrier are particularly preferred for making and using both preventive and therapeutic compositions. The term "topical" is used broadly to include both epidermal and/or skin surfaces, as well as mucosal surfaces of the body.

*B. coagulans* is non-pathogenic and is generally regarded as safe (i.e., GRAS classification by the U.S. Food and Drug Administration). The Gram positive rods have a cell diameter of greater than 1.0 µm with variable swelling of the sporangium, without parasporal crystal production.

1. Growth of *B. coagulans*

*B. coagulans* is aerobic and facultative, grown typically in nutrient broth, pH 5.7 to 6.8, containing up to 2% (by wt) NaCl, although neither NaCl nor KCl are required for growth. A pH of about 4 to about 6 is optimum for initiation of growth from spores. It is optimally grown at about 30° C. to about 55° C., and the spores can withstand pasteurization. It exhibits facultative and heterotrophic growth by utilizing a nitrate or sulphate source. Additional metabolic characteristics of *B. coagulans* are summarized in Table 1.

TABLE 1

| Characteristic | *B. coagulans* Response |
| --- | --- |
| Catalase production | Yes |
| Acid from D-Glucose | Yes |
| Acid from L-Arabinose | Variable |
| Acid from D-Xylose | Variable |
| Acid from D-Mannitol | Variable |
| Gas from Glucose | Yes |
| Hydrolysis of Casein | Variable |
| Hydrolysis of Gelatin | No |
| Hydrolysis of Starch | Yes |
| Utilization of Citrate | Variable |
| Utilization of Propionate | No |
| Degradation of Tyrosine | No |
| Degradation of Phenylalanine | No |
| Nitrate reduced to Nitrite | Variable |
| Allatoin or Urate Required | No |

*B. coagulans* can be grown in a variety of media, although it has been found that certain growth conditions produce a culture which yields a high level of sporulation. For example, sporulation is enhanced if the culture medium includes 10 milligrams per liter of manganese sulfate, yielding a ratio of spores to vegetative cells of about 80:20. In addition, certain growth conditions produce a bacterial spore which contains a spectrum of metabolic enzymes particularly suited for the present invention, i.e., control of microbial infections. Although spores produced by these particular growth conditions are preferred, spores produced by any compatible growth conditions are suitable for producing a *B. coagulans* useful in the present invention.

Suitable media for growth of *B. coagulans* include Nutristart 701, PDB (potato dextrose broth), TSB (tryptic soy broth) and NB (nutrient broth), all well known and available from a variety of sources. Media supplements containing enzymatic digests of poultry and fish tissue, and containing food yeast are particularly preferred. A preferred supplement produces a media containing at least 60% protein, and about 20% complex carbohydrates and 6% lipids. Media can be obtained from a variety of commercial sources, notably DIFCO (Detroit, Mich.), Oxoid (Newark, N.J.), BBL (Cockeyesville, Md.) and Troy Biologicals (Troy, Mich.).

A preferred procedure for preparation of *B. coagulans* is as follows. *B. coagulans* Hammer bacterium was inoculated and grown in nutrient broth containing 5 g Peptone, 3 g Meat extract, 10-30 mg $MnSO_4$ and 1,000 ml distilled water, adjusted to pH 7.0, using a standard airlift fermentation vessel at 30° C. The range of $MnSO_4$ acceptable for sporulation is 1 mg/l to 1 g/l. The vegetative cells can actively reproduce up to 65° C., and the spores are stable up to 90° C. After fermentation, the *B. coagulans* Hammer bacterial cells are collected using standard methods (e.g., filtration, centrifugation) and the collected cells and spores can be lyophilized, spray dried, air dried or frozen. As described herein, the supernatant from the cell culture can be collected and used as an extracellular agent secreted by B. coagulans which has antimicrobial activity useful in a formulation of this invention.

A typical yield from the above culture is about 100 to 150 billion cells/spores per gram before drying. Spores maintain at least 90% viability after drying when stored at room temperature for up to seven years, and thus the effective shelf life of a composition containing B. coagulans Hammer spores at room temperature is about 10 years.

2. Extracellular Products Having Antimicrobial Activity

B. coagulans cultures contain secreted products which have antimicrobial activity. These secreted products are useful in therapeutic compositions according to the present invention. Cell cultures are harvested as described above, and the culture supernatants are collected, by filtration or centrifugation, or both, and the resulting supernatant contains antimicrobial activity useful in a therapeutic composition. The preparation of a B. coagulans extracellular product is described in the Examples.

3. Sources of B. coagulans

Purified B. coagulans bacterium are available from the American Type Culture Collection (Rockville, Md.) using the following accession numbers: B. coagulans Hammer NRS T27 (ATCC# 11014), B. coagulans Hammer strain C (ATCC# 11369), B. coagulans Hammer (ATCC# 31284), and B. coagulans Hammer NCA 4259 (ATCC# 15949). Purified B. coagulans bacterium are also available from the Deutsche Sammlung von Mikroorganismen und Zellkuturen GmbH (Braunschweig, Germany) using the following accession numbers: B. coagulans Hammer $1915^{AL}$ (DSM# 2356), B. coagulans Hammer 1915' (DSM# 2383, corresponds to ATCC# 11014), B. coagulans Hammer$^{AL}$ (DSM# 2384, corresponds to ATCC# 11369), and B. coagulans Hammer$^{AL}$ (DSM# 2385, corresponds to ATCC# 15949). B. coagulans bacterium can also be obtained from commercial suppliers such as Sabinsa Corporation (Piscataway, N.J.).

These B. coagulans strains and their growth requirements have been described previously (Baker et al, Can. J. Microbiol. 6:557-563, 1960; Blumenstock, "Bacillus coagulans Hammer 1915 und andere thermophile oder mesophile, säuretolerante Bacillus-Arten-eine taxonomische Untersuchung", Doctoral thesis, Univ. Göttingen, 1984; Nakamura et al, Int. J. Syst. Bacteriol., 38:63-73, 1988). Strains of B. coagulans can also be isolated from natural sources (e.g., heat-treated soil samples) using well known procedures (Bergey's Manual of Systemic Bacteriology, Vol. 2, p. 1117, Sneath, P. H. A. et al., eds., Williams & Wilkins, Baltimore, Md., 1986). The results described herein were obtained with B. coagulans Hammer obtained from the American Type Culture Collection (ATCC# 31284) which was grown as described herein and stored in lyophilized aliquots at −20° C. All B. coagulans that exhibit the properties described herein are considered equivalents of this strain.

B. coagulans had previously been mischaracterized as a Lactobacillus in view of the fact that as originally described, this bacterium was labeled as Lactobacillus sporogenes (See Nakamura et al, cited above). However, this was incorrect because the bacterium of this invention produces spores and through metabolism excretes L(+)-lactic acid, both aspects which provide key features to its utility. Instead, these developmental and metabolic aspects required that the bacterium be classified as a lactic acid bacillus, and therefore it was renamed.

4. Probiotic Antimicrobial Activity of B. coagulans

Pathogenic bacteria inhibited by B. coagulans activity include Staphylococcus aureus, S. epidermidis, Streptococcus pyogenes, S. spp., Pseudomonas aeruginosa, Escherichia coli (enterohemorragic species), Clostridium perfingens, C. difficile, Gardnerella vaginalis, Propionibacterium acnes, Aeromonas hydrophilia, Aspergillus species, Proteus species and Klebsiella species. Pathogenic yeast and other fungus inhibited by B. coagulans activity include Candida albicans, C. tropicalis and Trichophyton mentagrophytes, T. interdigitale, T. rubrum, and T. yaoundei. B. coagulans activity also inhibits Herpes simplex viruses I and II. These pathogens can cause diaper rash, oral, genital, cervical and vaginal yeast infections, toxic shock syndrome, chronic mucocutaneous candidiasis, dermatophytosis, bacterial vaginosis, tineal fungal infections such as ringworm, athlete's foot and jock itch, scalp and nail fungal infections, superficial skin disorders such as erysipelas, open wound infections, acne, abscess, boil, eczema, dermatitis, contact dermatitis, hypersensitinitis, contact lesions, bed sores, diabetic lesions, miscellaneous opportunistic infections, oral and genital viral lesions, and the like conditions as are well known in the art. Therefore, topical use of compositions containing the B. coagulans active agents that inhibit these pathogens are useful in preventing or treating these conditions.

Antimicrobial activity of a therapeutic composition of this invention against many of the above-described pathogens is described in the Examples. In addition, it is contemplated that the present therapeutic compositions can be used, when formulated for administration to the relevant tissue, to treat infections as described below:

| Infecting Microbe | Condition |
|---|---|
| Trichophyton species | |
| T. mentagrophytes | tinea pedis, athlete's foot |
| T. interdigitale | tinea pedis, athlete's foot |
| T. mentagrophytes | tinea versicolor, ring worm |
| T. mentagrophytes | tinea barbae, face/neck inflammation |
| T. rubrum | dermatophytosis |
| T. yaoundei | Ring worm on scalp |
| Candida species | |
| C. albicans | systemic candidiasis |
| C. albicans | chronic mucocutaneous candidiasis, myositis and thymoma |
| C. albicans | yeast and mycelial phase infection |
| C. albicans | oral thrush |
| C. tropicalis | cervical yeast infection |
| Pseudomonas aeruginosa | opportunistic skin infections, urinary tract infections, post surgical infections |
| Staphylococcus aureus | opportunistic skin infections, abscess, boils, wound infections, dermatitis |
| Staphylococcus epidermidis | opportunistic skin infections |
| Streptococcus pyogenes | opportunistic skin infections, impetigo, erysipelas |
| Streptococcus spp. | opportunistic skin infections, wound infections |
| Gardnerella vaginalis | bacterial vaginosis |
| Propionibacterium acnes | acne |
| Clostridium perfringens | open wound infections |
| Herpes Simplex Virus I or II | cold sores, genital herpes lesions |

Other skin and mucous membrane infecting microbes and dermatophytes can also be treated using the present compositions and methods.

B. Fructooligosaccharides

Fructooligosaccharides (F'S) are a class of sugars particularly useful in the context of the present invention. F'S are a simple class of natural carbohydrates comprising polymers of fructose and glucose. FOS are non-digestible, fructose polymers that are utilized almost exclusively by the indigenous Bifidobacteria and *Lactobacillus* in the intestinal tract and can be similarly utilized by *Bacillus*. Deleterious bacteria such as *Clostridium, Staphylococcus, Salmonella* and *E. Coli* cannot metabolize FOS and therefor use of FOS in combination with *Bacillus* allows the beneficial and probiotic bacteria to grow and to replace any undesirable or pathogenic microorganisms.

The use of FOS in therapeutic compositions of the present invention provides a synergistic effect thereby increasing the effectiveness of the *Bacillus*-containing compositions of this invention. This synergy is manifest at least by increasing the ability of the bacterium to grow by increasing the food supplement for *Bacillus* which preferentially selects for growth of *Bacillus* over many other bacteria in the infected tissue. Thus, the presence of FOS in the formulation allows for more effective microbial inhibition by increasing the ability of *Bacillus* to grow and therefore provide its benefit.

FOS can be obtained from a variety of natural sources, including commercial suppliers. As a product isolated from natural sources, the components can vary widely and still provide the beneficial agent, namely FOS. FOS typically has a polymer chain length of from about 4 to 200 sugar units, with the longer lengths being preferred. For example, the degree of purity can vary widely so long as functional FOS is present in the formulation. Preferred FOS formulations contain at least 50% by weight of fructooligosaccharides compared to simple(mono or disaccharide) sugars such as glucose, fructose or sucrose, preferably at least 80% fructooligosaccharides, more preferably at least 90% and most preferably at least 95% fructooligosaccharides. Sugar content and composition can be determined by any of a variety of complex carbohydrate analytical detection methods as is well known.

Preferred sources of FOS include inulin, Frutafit IQ™ from Imperial Suiker Unie (Sugar Land, Tex.), NutraFlora™ from Americal Ingredients, Inc., (Anaheim, Calif.), Fabrchem, Inc., (Fairfield, Conn.), and Fruittrimfat Replacers and Sweeteners (Emeryville, Calif.).

C. Therapeutic Compositions

Compositions of this invention suitable for use in preventing, treating or controlling microbial infections comprise an active ingredient that is a *Bacillus* species bacterium (e.g., vegetative cell) or spore, *Bacillus coagulans, Bacillus coagulans* spores, extracellular antimicrobial or antibiotic metabolites of *B. coagulans*, or combinations thereof in various formulations.

The active *Bacillus* ingredients comprise about 0.1% to about 50% by weight of the final composition, preferably 1% to 10% by weight, in a formulation suitable for topical administration.

The formulation for a therapeutic composition of this invention may include other probiotic agents or nutrients for promoting spore germination and/or *Bacillus* growth. The compositions may also include known antimicrobial agents, known antiviral agents, known antifungal agents, all of which must be compatible with maintaining viability of the *Bacillus* active agent when *Bacillus* organisms or spores are the active agent. The other agents in the compositions can be either synergists or active agents. Preferably, the known antimicrobial, antiviral and/or antifungal agents are probiotic agents compatible with *Bacillus*. The compositions may also include known antioxidants, buffering agents, sunscreens and cosmetic agents, including coloring agents, fragrances, oils, essential oils, lubricants, moisterizers or drying agents. Antioxidants such as vitamin E may be included. Sunscreens such as para-aminobenzoic acid may be included. Lubricants such as synthetic or natural beeswax may also be included. Thickening agents may be added to the compositions such as polyvinylpyrrolidone, polyethylene glycol or carboxymethylcellulose.

Fragrances and essential oils are particularly suited for the compositions used in personal hygiene products and methods, and can include sea salts, herbs or herb extracts, fragrance oils from a large variety of plants or animals, and fragrances from a large variety of plants or animals, as are all well known.

Preferred fragrances useful in a composition of this invention include african violet, frankincense & myrrh, lavender, vanilla, gardenia, honeysuckle, sandlewood, musk, jasmine, lotus, orange blossom, patchouli, heather, magnolia, amber, rose, and the like fragrances.

Preferred oils, including essential or fragrant oils, include almond, aloe, amber, apple, apricot, bayberry, benzion, cactus blossom, carnation, carrageenan, cedarwood, cinammon, cloves, coconut, cedar, copal, emu, eucalyptus, franfipani, frankincense & myrrh, gardenia, grapefruit, heather, herbs, honeysuckle, jasmine, jojoba, kelp, lavender, lemon, lilac, lotus, magnolia, mulberry, musk, myrrh, narcissus, orange blossom, patchouli, peach, pinon pine, plumeria, rose, rosemary, safflower, sage, sandalwood, spirulina, strawberry, vanilla, violet, wisteria, and the like oils. A particularly preferred oil for use in a composition of the invention is emu oil, typically used in an amount of about 1% to 75% by weight.

In addition, the fragrances and essential oils can be provided in various bath salt and bath soap compositions. Salts and soaps are also well known in the art and can include sea salts, desert salts, mineral salts, sodium sesquicarbonate, magnesium sulfate, and the like commonly used bath salts.

Fragrances, oils and salts are well known in the art, can be obtained from a variety of natural and commercial sources, and are not considered to limiting to the invention. Exemplary commercial sources include Innovative Body Science (Carlsbad, Calif.), Scents of Paradise SunBurst Technology, Inc., (Salem, Oreg.), Intercontinental Fragrances, Inc., (Houston, Tex.), Scentastics, Inc., (Ft. Lauderdale, Fla.), Michael Giordano International, Inc., (North Miami, Fla.).

Chemicals used in the present compositions can be obtained from a variety of commercial sources, including Spectrum Quality Products, Inc (Gardena, Calif.), Seltzer Chemicals, Inc., (Carlsbad, Calif.) and Jarchem Industries, Inc., (Newark, N.J.).

The active agents are combined with a carrier that is physiologically compatible with the skin, membrane or mucosal tissue of a human or animal to which it is topically administered. That is, the carrier is preferably substantially inactive except for surfactant properties used in making a suspension of the active ingredients. The compositions may include other physiologically active constituents that do not interfere with the efficacy of the active agents in the composition.

A typical therapeutic composition will contain in a one gram dosage formulation from $10^3$ to $10^{12}$, preferably $2\times10^5$ to $10^{10}$, colony forming units (CFU) of viable *Bacillus* bacteria (i.e., vegetative cell) or bacterial spore. In one preferred embodiment a therapeutic composition may include from about 10 milligrams (mg) to one gram of fructooligosaccharides. The formulation may be completed in weight using any of a variety of carriers and/or binders. A preferred carrier is micro-crystalline cellose (MCC) added in an amount sufficient to complete the one gram dosage total weight.

Particularly preferred formulations for a therapeutic composition of this invention are described in the Examples.

Carriers can be solid-based dry materials for formulations in powdered form, and can be liquid or gel-based materials for formulations in liquid or gel forms, which forms depend, in part, upon the routes or modes of administration.

Typical carriers for dry formulations include trehalose, malto-dextrin, rice flour, micro-crystalline cellulose (MCC), magnesium sterate, inositol, FOS, gluco-oligosaccharides (GOS), dextrose, sucrose, talc, and the like carriers.

Where the composition is dry and includes evaporated oils that produce a tendency for the composition to cake (adherence of the component spores, salts, powders and oils), it is preferred to include dry fillers which distribute the components and prevent caking. Exemplary anti-caking agents include MCC, talc, diatomaceous earth, amorphous silica and the like, typically added in an amount of from about 1 to 95% by weight.

Suitable liquid or gel-based carriers are well known in the art, such as water and physiological salt solutions, urea, alcohols and glycols such as methanol, ethanol, propanol, butanol, ethylene glycol and propylene glycol, and the like. Preferably, water-based carriers are about neutral pH.

Suitable carriers include aqueous and oleaginous carries such as, for example, white petrolatum, isopropyl myristate, lanolin or lanolin alcohols, mineral oil, fragrant or exxential oil, nasturtium extract oil, sorbitan mono-oleate, propylene glycol, cetylstearyl alcohol (together or in various combinations), hydroxypropyl cellulose (MW=100,000 to 1,000,000), detergents (e.g., polyoxyl stearate or sodium lauryl sulfate) and mixed with water to form a lotion, gel, cream or semi-solid composition. Other suitable carriers comprise water-in-oil or oil-in-water emulsions and mixtures of emulsifiers and emollients with solvents such as sucrose stearate, sucrose cocoate, sucrose distearate, mineral oil, propylene glycol, 2-ethyl-1,3-hexanediol, polyoxypropylene-15-stearyl ether and water. For example, emulsions containing water, glycerol stearate, glycerin, mineral oil, synthetic spermaceti, cetyl alcohol, butylparaben, propylparaben and methylparaben are commercially available. Preservatives may also be included in the carrier including methylparaben, propylparaben, benzyl alcohol and ethylene diamine tetraacetate salts. Well-known flavorings and/or colorants may also be included in the carrier. The composition may also include a plasticizer such as glycerol or polyethylene glycol (MW=800 to 20,000). The composition of the carrier can be varied so long as it does not interfere significantly with the pharmacological activity of the active ingredients or the viability of the *Bacillus* cells or spores.

A therapeutic composition can be formulated to be suitable for application in a variety of ways, for example in a cream for skin (e.g., ringworm or athlete's foot), in a wash for the mouth (e.g., oral thrush), in a douche for vaginal application (e.g., vaginitis), in a powder for chaffing (e.g., dermatitis), in a liquid for toe nails (e.g., tinea pedis), in a bath salt or bath powder for treating genital, foot or other tissue infections in a bath, and the like as described in more detail in the Examples. Other formulations will be readily apparent to one skilled in the art.

D. Therapeutic Methods for Treating Microbial Infections

The present invention contemplates a method for treating, reducing or controlling microbial infections in a variety of skin and mucosal membrane tissues using a therapeutic composition or therapeutic article of manufacture of this invention. Optimally the compositions effectively reduce the yeast, fungal and/or viral titre in the treated individual, particularly at the site of application of the topical composition. For example, the pathogenic microbial titre in lesions is significantly reduced with topical treatment of affected areas of the skin or mucous membrane. The disclosed methods of treatment also reduce symptoms of pathogenic microbial infection (e.g., pain associated with infected or microbial-caused lesions) and promote more rapid healing than seen without *Bacillus* treatment.

The method of the present invention includes administration of a composition containing the active *Bacillus* ingredient to a human or animal to treat or prevent microbial, i.e, bacterial, yeast, fungal or viral, infection. Administration is preferably to the skin or a mucous membrane using a cream, lotion, gel, oil, ointment, suspension, aerosol spray, powder, semi-solid formulation (e.g., a suppository), or article of manufacture, all formulated to contain a therapeutic composition of this invention using methods well known in the art.

Application of the compositions containing the active *Bacillus* agent effective in preventing or treating a microbial infection generally consist of one to ten applications of 10 mg to 10 g of a composition per application for one day up to one month. Applications are generally once every twelve hours and up to once every four hours. Preferably two to four applications of the composition per day, of about 0.1 g to 5 g per application, for one to seven days are sufficient to prevent or treat a microbial infection. For topical applications, the compositions are preferably applied to lesions daily as soon as symptoms (e.g., pain, swelling or inflammation) are detected. Of course, the specific route, dosage and timing of the application will depend, in part, on the particular pathogen and/or condition being treated and the extent of the condition.

A preferred method involves the application of from $10^3$ to $10^{12}$ viable bacterium or spore per day, preferably from $10^5$ to $10^{10}$, and more preferably about from $5\times10^8$ to $10^9$ viable bacterium or spore per day. In addition, a preferred method optionally comprises application of a composition that additionally contains from 10 mgs to 20 gms of fructooligosaccharide per day, preferably about 50 mg-10 gm, and more preferably about from 150 mgs to 5 gms of fructooligosaccharide per day, to promote growth of the probiotic *Bacillus* species over the growth of the pathogen.

In the case of a therapeutic bath, one embodiment provides for the addition and admixing of a composition of dry *Bacillus* spores to a prepared bath that may contain soaps, oils, fragrances, salts, and the like bath components, followed by contacting the infected tissue to the bath water, as by "taking a bath" in the conventional sense. In this embodiment, the therapeutic probiotic spores can be packaged in a system with instructions as described herein. A typical bath would provide $10^8$ to $10^{10}$ CFU of bactial cells or spores, preferably about $1\times10^9$ to $5\times10^9$ CFU of cells or spores per bath.

Specific methods for treating a microbial infection are described in the Examples, and include diaper rash, vaginal yeast infection, opportunistic skin infection, tineal fungal infection, superficial skin infection, acne, cold sores, genital Herpes lesions, athlete's foot, and the like.

Unless defined otherwise, all scientific and technical terms used herein have the same meaning as commonly understood by those skilled in the relevant art. Unless mentioned otherwise, the techniques employed or contemplated herein are standard methodologies well known to one of ordinary skill in the art. The examples of embodiments are for illustration only.

E. Therapeutic Systems for Treating Microbial Infections

The invention further contemplates a therapeutic system for treating, reducing and/or controlling microbial infections comprising a container comprising a label and a therapeutic composition according to the present invention, wherein said label comprises instructions for use of the composition for treating said infection.

Typically, the system is present in the form of a package containing a therapeutic composition of this invention, or in combination with packaging material. The packaging material includes a label or instructions for use of the components of the package. The instructions indicate the contemplated use of the packaged component as described herein for the methods or compositions of the invention.

For example, a system can comprise one or more unit dosages of a therapeutic composition according to the invention. Alternatively, the system can contain bulk quantities of a therapeutic composition. The label contains instructions for using the therapeutic composition in either unit dose or in bulk forms as appropriate, and may include information regarding storage of the composition, disease indications, dosages, routes and modes of administration and the like information.

Furthermore, depending upon the particular contemplated use, the system may optionally contain either combined or in separate packages one or more of the following components: FOS: bath salts, soaps and oils (for a bath use), and the like components. One particularly preferred system comprises unit dose packages of *Bacillus* spores for use in combination with a conventional bath salt or bath soap product, together with instructions for using the *Bacillus* probiotic in a therapeutic method.

F. Articles of Manufacture

The invention also contemplates various articles of manufacture which utilize the beneficial aspects of the present invention by combination of the therapeutic composition with various medical or personal hygiene devices so as to reduce or prevent microbial infections associated with the use of these devices. The invention comprises compositions of *Bacillus* and/or isolated *B. coagulans* active agent applied to a solid surface or impregnated into a solid matrix of any device or article of manufacture that is intended to be in contact with skin or a mucous membrane. Preferably the solid surface is a flexible article than can be worn on or wiped on the skin or mucous membrane. More preferably, when the flexible item carrying the *Bacillus* and/or the isolated active agent is to be worn on the skin it includes a means for attaching the article to the skin such as, for example, an adhesive layer, interengaging hook and pile (Velcro®) connectors, or other well known means of attachment such as ties, snap closures, elastic, buttons and the like.

Specific embodiments which include *Bacillus* and/or isolated *B. coagulans* active agent are diapers, towelettes (e.g., baby wipes or feminine hygiene towelettes), tampons, dermal patches, adhesive tape, absorbent pads, articles of clothing (e.g., underclothes, sleeping apparel), bath towels, wash cloths, and the like. The article may be made of fibrous woven, knitted or nonwoven materials, occlusive or nonocclusive films or membranes, synthetic polymer fibers, films, membranes and foams (e.g., nylon, polytetrafluoroethylene (PTFE, such as Teflon® or Gor-Tex®), polystyrene, polycarbonate, polyvinylchloride and polysulphone). All of these forms are well known in the art and include, for example, knitted or woven fabrics, nonwoven fabrics such as felt and batting, fiber balls of cotton, rayon, cellulose or synthetic fibers and the like materials.

The *Bacillus* and/or *B. coagulans* isolated active agent can be applied to the solid surface using any of a variety of known methods including, for example, applying a powder, spray drying the probiotic onto the material or soaking the material in a solution containing the probiotic and then using the wetted material or drying the material before use. Porous material may contain the *Bacillus* and/or the isolated active agent in the pores or interstices of the solid material. The *Bacillus* and/or the isolated active agent can be attached by adhesion, such as by attachment to an adhesive layer that is then applied to the skin (e.g., in a bandage or dermal patch). The *Bacillus* and/or the isolated active agent can be impregnated into the solid material during the manufacturing process of the flexible article (e.g., added to a synthetic composition before or during the polymerization process). The pressure and heat resistance of *Bacillus* spores makes them particularly suitable for incorporation into the material during manufacturing. Any of the solid materials carrying *Bacillus* and/or the isolated active agent can be packaged individually or in groups, suitable for holding the treated material using standard packaging materials (e.g., in a shrink wrapper, sealed packet, protective wrapper or dispensing container suitable for holding dry or wet materials).

The article of manufacture can have applied thereon any of the additional/optional components of a therapeutic composition of this invention, including carriers, salts, FOS, fragrances, and the like.

Any of a variety of methods for placing the therapeutic composition onto a subject article can be used, and therefor the invention need not be so limited. However, preferred methods include a "spray-dry" method in which the material is exposed in a low humidity chamber to an atomized mix containing a liquid composition, where the chamber is subsequently exposed to about 80-110 degrees Fahrenheit to dry the liquid, thereby impregnating the material of the article with the components of the composition. A typical load is from $10^5$ to $10^9$ cfu of bacteria/spores per ml of atomizing mix, to place that same amount on about one square inch of external surface of fibrous carrier/article material. The dry article is then ready for storage in a sterile package for use.

EXAMPLES

The following examples relating to this invention are illustrative and should not, of course, be construed as specifically limiting the invention. Moreover, such variations of the invention, now known or later developed, which would be within the purview of one skilled in the art are to be considered to fall within the scope of the present invention hereinafter claimed.

Example 1

Antimicrobial Activity of *B. coagulans*

The ability of *B. coagulans* to inhibit various fungal pathogens was demonstrated using an in vitro assay. The tested fungal strains of *Trichophyton* species are available from the American Type Culture Collection (ATCC) (Rockville, Md.) and their ATCC accession numbers are shown in Table 2. In the assay, potato-dextrose plates (DIFCO®, Detroit, Mich.) were prepared using standard procedures and were inoculated individually with a confluent bed (about $1.7 \times 10^6$) of various species of the fungus *Trichophyton*. Inhibition by B. coagulans was tested by placing on the plate about $1.5 \times 10^6$ colony forming units (CFU) in 10 µl of broth or buffer, plated directly in the center of the potato-dextrose plate with one test locus per plate. The size of each test locus was about 8 mm in diameter and a minimum of three tests were performed for each inhibition assay. The negative control was a 10 µl drop of sterile saline solution, and the positive control was a similar volume of 2% miconazole (1-[2-(2,4-dichlorophenyl)-2-[(2, 4-dichlorophenyl)methoxy]ethyl]-1H-imidazole in an inert cream. The plates were then incubated for about 18 hr at 30° C. when the zone of inhibition was measured. As used herein, "excellent inhibition" means the zone was 10 mm or greater in diameter; and "good inhibition" means the zone was greater than 2 mm in diameter but less than 10 mm in diameter.

The results of in vitro inhibition by B. coagulans are shown in Table 2. For each of the Trichophyton species tested, the disease condition associated with an infection is indicated in column 2 of Table 2. For comparison, no zone of inhibition was seen with the negative control. Good inhibition (about 8.5 mm diameter, mean average of three tests) was seen with the positive control.

TABLE 2

| Pathogen | Related Disease | Inhibition Results |
| --- | --- | --- |
| T. mentagrophytes (ATCC# 4808) | Tinea pedis (Athlete's Foot) | Excellent |
| T. interdignale (ATCC# 9129) | Tinea pedis (Athlete's Foot) | Excellent |
| T. mentagrophytes (ATCC# 36107) | Tinea versicolor (Ring Worm) | Excellent |
| T. mentagrophytes (ATCC# 8125) | Tinea barbae (Face & Neck Inflammation) | Good |
| T. mentagrophytes (ATCC# 9533) | Tinea pedis | Excellent |
| T. mentagrophytes (ATCC# 28187) | Tinea pedis | Excellent |
| T. rubrum (ATCC# 18753) | Mild Dermatophytosis | Good |
| T. yaoundei (ATCC# 13947) | Ring Worm, Scalp | Good |

Similarly, the ability of B. coagulans to inhibit various yeast pathogens was demonstrated in vitro for four species of Candida, all of which are available from the American Type Culture Collection (Rockville, Md.) with their ATCC accession numbers shown in Table 3. In the assay, potato-dextrose plates (DIFCO®, Detroit, Mich.) were prepared using standard procedures and were inoculated individually with a confluent bed about $1.7 \times 10^6$ of the four species of Candida. Inhibition by B. coagulans was tested by placing on the plate about $1.5 \times 10^6$ CFU in 10 µl of broth or buffer, plated directly in the center of the potato-dextrose plate with one test locus of about 8 mm in diameter per plate. A minimum of three tests were performed for each inhibition assay. The negative control was a 10 µl drop of a sterile saline solution and the positive control was a 10 µl volume of miconazole cream. The plates were then incubated for about 18 hr at 30° C. when the zone of inhibition was measured using the same criteria as defined earlier herein. No inhibition was seen with the negative control and good inhibition (about 8.7 mm diameter, average of three tests) was seen with the positive control.

The results of the in vitro tests are shown in Table 3 with the pathological conditions in humans associated with infection by the Candida species shown in column 2.

TABLE 3

| Species | Pathology | Inhibition Results |
| --- | --- | --- |
| Candida albicans (ATCC# 26555) | Chronic Mucocutaneous, Candidiasis, Myositis and Thymoma | Excellent |
| C. albicans (ATCC# 44203) | Systemic Candidiasis | |
| Excellent | C. albicans (ATCC# 44807) | |
| Yeast and Mycelial Phase | Excellent | C. tropicalis (ATCC# 62377) |
| Cervical Yeast Infection | Excellent | |

Similarly, the ability of B. coagulans to inhibit opportunistic bacterial pathogens was demonstrated in vitro for Pseudomonas aeruginosa and Staphylococcus aureus which are part of a standard bacterial pathogen screen (U.S. Food and Drug Administration) and are commercially available on solid support disks (DIFCO® BACTROL® disk set). In the assay, potato-dextrose plates (DIFCO®) were prepared using standard procedures and were inoculated individually with a confluent bed $1.5 \times 10^6$ of each of the four species of bacteria. Inhibition by B. coagulans was tested by placing on the plate about $1.5 \times 10^6$ CFU in 10 µl of broth or buffer, plated directly in the center of the potato-dextrose plate with one test locus of about 8 mm in diameter per plate. A minimum of three test loci were used for each assay. The negative control was a 10 µl drop of a sterile saline solution and the positive control was a 10 µl volume of glutaraldehyde. The plates were then incubated for about 18 hr at 30° C. when the zone of inhibition was measured using the same criteria as defined earlier herein. No inhibition was seen with the negative control and excellent inhibition (about 16.2 mm diameter, average of three tests) was seen with the positive control. Excellent inhibition was also seen for both opportunistic pathogens, P. aeruginosa and S. aureus.

Example 2

Formulation of a Therapeutic Composition

Formulation 1: Bathing Formulation (Per Bath/Dosage)

| | |
| --- | --- |
| B. coagulans | 250,000,000 spores (~18 mg) |
| bath salts (sea & mineral salts) | 10 gm |
| fructooligosaccharides (FOS) | 1 gm |
| micro-crystalline cellulose (MCC) | 5 gm |
| fragrance | Trace |

Formulation 2: Topical Ointment (Per ml)

| | |
| --- | --- |
| B. coagulans extract (Example 3B) | 100 ul |
| lanolin | 780 ul |
| Emu oil | 100 ul |
| geranium essential oil | 20 ul |
| fragrance | trace |

Formulation 3: Topical Liquid for Dropper Application (Per ml)

| | |
| --- | --- |
| B. coagulans extract (Example 3B) | 500 ul |
| Emu oil | 450 ul |
| geranium essential oil | 20 ul |
| Tween-80 detergent | 30 ul |
| fragrance | trace |

Formulation 4: Powder (Per Gram)

| B. coagulans | 100,000,000 spores (~8 mg) |
|---|---|
| talc | 992 mg |
| powdered lavender fragrance | trace |

Example 3A

Preparation of B. coagulans Spores

A culture of dried B. coagulans spores was prepared as follows. Ten million spores were innoculated into a one liter culture containing 24 gms potato dextrose broth, 10 gms of enzymic digest of poultry and fish tissue, 5 gms of FOS and 10 gms MnSO4. The culture was maintained for 72 hours under a high oxygen environment at 37 degrees Centigrade to produce culture having about 150 billion cells per gram of culture. Thereafter, the culture was filtered to remove culture medium liquid, and the bacterial pellet was resuspended in water and freeze-dried. The freeze-dried powder is then ground to a fine powder using standard good manufacturing practice (GMP). The powder is then combined into Formulation 1 or Formulation 4 as described in Example 2 to form dry powder compositions.

Example 3B

Preparation of *B. coagulans* Extracellular Products

A one liter culture of *B. coagulans* was prepared as described in Example 3A except the FOS was omitted. The culture was maintained for 5 days as described, at which time FOS was added at 5 gm/liter, and the culture was continued. 20 ml of carrot pulp was then added at day 7, and the culture was harvested when the culture became saturated (no substantial cell division). The culture was first autoclaved for 30 minutes at 250 degrees Farenheight, and then centrifuged at 4000 rpm for 15 min. The resulting supernatant was collected and filtered in a Buchner funnel through a 0.8 micron (u) filter, and the filtrate (pass through) was collected and further filtered through a 0.2 u Nalge vacuum filter. The resulting pass-through was collected (about 900 milliliters) to form a liquid containing an extracellular product, and used in inhibition studies.

Following the assay described in Example 1 using *Candida albicans*, one milliliter of the above-produced extracellular product was added to the test plate in place of the bacterium. After the same culturing time, a zone of inhibition of about 10 to 25 millimeters was observed, indicating a potent antimicrobial activity of "excellent" quality, using the terminology of Example 1.

The liquid containing the extracellular product was formulated into a liquid ointment composition for use in direct application onto a tissue using a dropper, such as would be convenient to treat a fungal infection of the toe nail. This liquid ointment was prepared by combining the liquid extracellular product produced above with Emu essential oil in a ratio of about 8:2, and trace fragrances were added to produce an aesthetic component.

Alternatively, one can use any liposomal or oil based transdermal delivery component in place of the Emu oil. The typical ratio of probiotic extracellular product to carrier or delivery component is a range of from about 1 to 90% probiotic, and preferably about 10 to 75% probiotic.

Example 4

Topical Application to Prevent Diaper Rash

A powder, aerosol spray liquid, or aerosol spray powder containing *B. coagulans* active agent, preferably *B. coagulans* spores, is applied to diapers by the consumer before use. Alternatively, disposable diapers supplied from the manufacturer may contain *B. coagulans* active agent, preferably *B. coagulans* spores, impregnated into the diaper material where it would be adjacent to the child's skin when in use. When the diaper becomes wetted by urine and/or fecal material, the spores are activated, usually within about twenty minutes. *B. coagulans* spore germination and *B. coagulans* growth after spore germination produce sufficient antifungal, including anti-yeast, activity to inhibit growth of yeast and fungal organisms in the diapers and on the child's skin, thus preventing diaper rash or other diaper-associated opportunistic infections.

Alternatively or in addition to treating diapers with *B. coagulans*, the child's skin in the diaper area can be treated with a saturated soft cloth wipe, powder, aerosol spray liquid, aerosol spray powder, lotion, cream or ointment containing *B. coagulans* active agent. Optimally, the *B. coagulans* formulation is applied to the child's skin after bathing and/or when the diapers are changed.

Suitable formulations include a powder of talc and optionally fragrance containing about $10^5$ to about $10^{10}$ *B. coagulans* spores per gram. Other suitable powder formulations contains talc, mineral oil, magnesium carbonate, DMDM hydantoin and about $10^5$ to about $10^{10}$ *B. coagulans* spores per gm or about $10^5$ to about $10^{10}$ *B. coagulans* spores per gm of a corn starch and calcium carbonate powder. An aerosol powder that includes an isobutane or other well known propellant made using standard methods is also suitable. An aerosol spray may be formulated by combining about $10^6$ to about $10^{11}$ *B. coagulans* spores per gm in isopropyl myristate, about 60% (w/w) SD alcohol 40-B, and isobutane as the propellant using standard methods. A manual pump spray containing about $10^5$ to about $10^{11}$ *B. coagulans* spores per gm of a neutral aqueous solution with no chemical propellant is also suitable. A suitable spray formulation includes alcohol, glycerin, purified water and methylparaben in addition to the *B. coagulans* probiotic. A cream formulation includes aloe vera gel, isopropyl myristate, methylparaben, polysorbate 60, propylparaben, purified water, sorbitan monostearate, sorbitol solution, stearic acid and about $10^5$ to about $10^{10}$ *B. coagulans* spores per gm. Another protective cream contains vitamins A and D equivalent to the concentration found in cod liver oil, cetylpalmitate, cotton seed oil, glycerin, glycerol monostearate, optional fragrance, methylparaben, mineral oil, potassium stearate, propylparaben and about $10^5$ to about $10^{10}$ *B. coagulans* spores per gm. An ointment contains cod liver oil, lanolin oil, methylparaben, propylparaben, talc, optional fragrance and about $10^5$ to about $10^{10}$ *B. coagulans* spores per gm. Another ointment formulation includes petrolatum, water, paraffin, propylene glycol, milk protein, cod liver oil, aloe vera gel, optional fragrance, potassium hydroxide, methyl paraben, propyl paraben, vitamins A, D and E and about $10^5$ to about $10^{10}$ *B. coagulans* spores per gm. A soft cloth pad (i.e., a baby wipe) is soaked in an aqueous solution (e.g., water, amphoteric 2, aloe vera gel, DMDM hydantoin or an aqueous solution of 30%-70% alcohol) and about $10^4$ to about $10^9$ B. coagulans spores per gm.

Example 5

Topical Treatment of Vaginal Yeast Infection

Bath products, including granulated or powdered bubble bath, bath crystals, bath salts, bath oils, powders, aerosol microparticulates and the like, for treatment of vaginal Candida albicans and/or C. tropicalis infections are produced in any of a variety of well-known formulations containing B. coagulans spores as follows. For bubble baths, bath crystals, bath salts, bath oils and the like which are placed in bath water, about $5\times10^9$ B. coagulans spores are used per standard bath (about 30 to 100 gal), such that a bath powder composition comprises about $150-200\times10^6$ spores per gram of powder. For chaffing (talc-type) powders, about $1\times10^9$ B. coagulans spores per gm of talc, powdered oatmeal, cornstarch or similar powdered substance are used. For aerosols of microparticulates, about $1\times10^9$ B. coagulans spores per ml of carrier are used.

A bath oil contains about $10^9$ B. coagulans spores per ml of an oil based formulation such as mineral oil, laureth-4, quaternium-18 hectorite and phenylcarbinol. Natural oil based formulations containing about $10^9$ B. coagulans spores per ml of a mixture that includes, for example, olive oil, grape seed oil, emu oil, sweet almond oil, geranium oil, grapefruit oil, mandarin oil and peppermint oil are also suitable, with or without fragrance.

A suitable nonsoap emollient cleanser includes sodium octoxynol-2 ethane sulfonate solution in water, petrolatum, octoxynol-3, mineral oil or lanolin oil, cocamide MEA, optional fragrance, imidazolidinyl urea, sodium benzoate, tetrasodium EDTA, methylcellulose, adjusted to pH 6.5 to 7.5, and about $10^7$ to about $10^{10}$ B. coagulans spores per gin. Other suitable cleansers include well known water, glycerin and sodium oleate based formulas, adjusted to about pH 7.0, and containing about $10^7$ to about $10^{10}$ B. coagulans spores per gm. Hard milled soaps made by standard methods may also include about $10^7$ to about $10^{10}$ B. coagulans spores/g because the spores can withstand pressure and heat during soap manufacturing.

A soft cloth towelette soaked in a solution of water, potassium sorbate, disodium EDTA and containing about $10^6$ to about $10^9$ B. coagulans spores per towelette can be used to clean the external vaginal area. Additional components to the formulation may include DMDM hydantoin, isopropyl myristate, methylparaben, polysorbate 60, propylene glycol, propylparaben or sorbitan stearate. The disposable towelette is used to gently wipe the perivaginal area and then discarded.

In addition, vaginal suppositories or inserts containing about $1\times10^8$ B. coagulans spores in an inert solid formulation are useful for mucosal treatment of C. albicans and/or C. tropicalis infections. Such formulations are well known in the art and can be made, for example, from a combination of corn starch, lactose, a metal stearate (e.g., magnesium stearate) and povidone. One to three inserts should be used per day while symptoms (e.g., vaginal itch and/or whitish discharge) are detected, with optimally about one insert per day used for a total of three to seven days, preferably at bedtime.

Example 6

Prevention and/or Treatment of Opportunistic Skin Infections

Opportunistic skin infections with Pseudomonas and or Staphylococcus species (typically P. aeruginosa, S. epidermidis, S. aureus) commonly occur in conjunction with skin allergies (e.g., allergic reactions to plant irritants such as poison ivy), bed sores, diabetic lesions or other types of skin lesions. Probiotic formulations containing B. coagulans spores ($10^5$ to $10^{10}$/ml depending on the formulation and the application) and/or supernatant or filtrate containing extracellular bacteriocins produced by B. coagulans are useful for preventing or treating opportunistic skin pathogens. Additionally, probiotic B. coagulans formulations are useful to prevent infection with methicillin-resistant Staphylococcus aureus (MRSA), particularly following injury or surgical incisions. A water-in-oil or oil-in-water emulsion, cream, lotion, powder, aerosol powder, or aerosol spray containing about $1\times10^6$ to about $1\times10^9$ B. coagulans spores per ml is used. Some suitable carriers are described herein, and others are well known in the art.

The skin is cleaned with soap and water and dried thoroughly. Then the B. coagulans containing formulation is applied to the skin, making sure that the formulation reaches between toes, under breasts, under arms, or other areas where the skin may become moist or exhibit friction chafing.

In addition to treating the skin topically with an emulsion, cream, lotion, powder, aerosol powder, or aerosol spray containing B. coagulans probiotic, the skin may be cleansed with a probiotic formulation such as described herein.

Example 7

Treatment of Tineal Fungal Infections

Ringworm (tinea versicolor) is caused by localized infections of the skin of the trunk and neck by dermatophyte fungus which colonizes the outer layer of the skin resulting in generally circular patches of white, brown or pink flaking skin that are often itchy. Once ringworm is detected, the affected area and a surrounding about 1 to 10 cm² area is treated twice daily with a cream or lotion containing 10% by weight B. coagulans spores. Suitable carriers are described herein, optimally containing about 110 to about $10^{10}$ B. coagulans spores per ml of carrier.

For treatment of tinea cruris (jock itch), a powder containing about $10^7$ to about $10^9$ B. coagulans spores per ml of colloidal silicon dioxide, isopropyl myristate, talc and optional fragrance is applied to the groin area to provide relief of itching, chafing, burning rash and irritation. Treatment is twice daily, generally after bathing and at bedtime, until symptoms are no longer detected.

Clothing, particularly underclothes and nightclothes that come in contact with the trunk and neck are sprayed with an aerosol containing about 1% to about 20% B. coagulans active agent in a suitable carrier such as described herein to prevent the spread of the infection to additional areas of the body.

Example 8

Treatment of Superficial Skin Infections

Superficial infections with Staphylococcus species (e.g., S. aureus, S. epidermidis) of a blocked sweat or sebaceous gland cause pustules, boils, abscesses, styes or carbuncles. These superficial skin infections may be accompanied by a blistering rash, particularly in babies, due to bacterial toxins released by the *Staphylococcus* species.

A water-in-oil or oil-in-water emulsion, cream, lotion, or gel, containing about $1\times10^6$ to about $1\times10^9$ *B. coagulans* spores per ml may be used. An exemplary topical gel is prepared by mixing together equal volumes of propylene glycol and water, 1% by weight hydroxypropyl cellulose (MW 100,000 to 1,000,000) and lyophilized *B. coagulans* culture to a final concentration of $1\times10^6$ to about $1\times10^9$ *B. coagulans* spores per ml of the combination, and allowing the stirred mixture to sit for 3 to 5 days to form a gel. Other formulations are presented herein.

The *B. coagulans*-containing emulsion, cream, lotion, or gel is applied to the area of the skin showing superficial skin infections (pustules, boils, abscesses, styes or carbuncles) or rash and gently rubbed into the skin and allowed to air-dry. Applications are at least once per day, preferably two to three times per day (e.g., morning and night), or after each washing of the infected area for those areas which are washed frequently (e.g., the hands or diaper area). Applications are continued until skin inflammation has subsided and the skin appears normal to the observer. In cases where scabbing has occurred in the infected area, once daily applications are continued until the scabs are no longer present.

Example 9

Acne Treatment

For treatment or prevention of acne vulgaris, a cleanser containing *B. coagulans* active ingredient obtained from a supernatant of bacterial culture is applied daily as a skin care product for removing excess dirt and oil and for preventing opportunistic infection of the skin. A suitable cleanser includes bentonite, cocoamphodipropionate, optional fragrance, glycerin, iron oxides, magnesium silicate, sodium borohydride, sodium chloride, sodium cocoate, sodium tallowate, talc, tetrasodium EDTA, titanium dioxide, trisodium HEDTA, water and about 1% to about 20% (v/v) of an aqueous supernatant or filtrate of a *B. coagulans* culture grown to saturation.

A similar cleanser, particularly for sensitive skin, includes about 30-50% colloidal oatmeal, suspended in a base of water, glycerin, distearyldimonium chloride, petrolatum, isopropyl palmitate, cetyl alcohol, dimethicone, sodium chloride, adjusted to pH about 7.0, and containing about 5% to about 50% (v/v) of an aqueous supernatant or filtrate of a *B. coagulans* culture grown to saturation.

Alternatively, the skin may be cleansed using any well known cleanser and then a cream containing *B. coagulans* active ingredient from a culture supernatant or filtrate is applied to the skin in a thin film about once every two days to about three times daily as needed. A suitable cream includes about 10-12% alcohol (w/w) bentonite, optional fragrance, iron oxides, potassium hydroxide, propylene glycol, titanium dioxide, purified water and about 0.5% to about 60% (v/v) of an aqueous supernatant or filtrate of a *B. coagulans* culture grown to saturation.

The above formulation is suited for treating acne caused by *Propioni bacterium* acne and by *Staphylococcus epidermidis*.

Example 10

Treatment of Cold Sores or Genital Herpes Lesions

Cold sores, generally around or in the mouth are caused by the virus Herpes simplex I. Similar lesions around the genitals are caused by Herpes simplex II. Herpes simplex infections can also cause painful finger or toe swelling (Whitlow). Both types of Herpes simplex lesions or Whitlow can be treated with a cream, lotion or gel ointment containing about $1\times10^7$ to about $1\times10^{10}$ *B. coagulans* spores per ml.

For oral cold sores, a soothing emollient lip balm contains allantoin, petrolatum, titanium dioxide at cosmetically acceptable levels, and about $10^7$ to about $10^{10}$ *B. coagulans* spores per ml. The lip balm may further include a sunscreen (e.g., padimate O). An alternative emollient lip balm contains the same base ingredients mixed to form an emulsion with 0.5% to 20% (v/v) of an aqueous supernatant or filtrate of a *B. coagulans* culture grown to saturation. The lip balm is applied to the lips and affected area to form a light film as a prophylactic when prodromal symptoms are felt (tingling, itching, burning) or when a lesion is visible. The lip balm should be applied as often as needed (e.g., every hour when a lesion is present) and generally once per day at bedtime.

For oral cold sores, the *B. coagulans* spores or extracellular agent in culture supernatant or filtrate may be formulated into a semisolid lip balm containing about 20-40% white petrolatum, wax paraffin, mineral oil, isopropyl lanolate, camphor, lanolin, isopropyl myristate, cetyl alcohol, carnuba wax, methylparaben, propylparaben, titanium dioxide and optionally fragrance and coloring agents.

For genital herpes lesions, a cream or ointment is formulated using standard methods as described herein containing about $1\times10^7$ to about $1\times10^{10}$ *B. coagulans* spores per ml and/or 0.5% to 20% (v/v) of an aqueous supernatant or filtrate of a *B. coagulans* culture grown to saturation. The cream or ointment is applied at least twice daily as needed.

Example 11

Ear Props or Ear Wash Containing *B. coagulans* Spores

For prevention or treatment of outer ear canal infections, an aqueous formulation that includes about $1\times10^5$ to about $1\times10^8$ *B. coagulans* spores per ml and/or 0.1% to 15% (v/v) of an aqueous supernatant or filtrate of a *B. coagulans* culture grown to saturation is used. The spores and/or supernatant is added to a sterile aqueous solution of 5-50% glycerin, 0.1-5% propylene glycol and sodium stannate or sodium chloride. An alternative formulation includes about $1\times10^5$ to about $1\times10^8$ *B. coagulans* spores per ml and/or 0.1% to 15% (v/v) of an aqueous supernatant or filtrate of a *B. coagulans* culture grown to saturation in a sterile aqueous solution of 0.5-25% glycerin, 5-10% alcohol and polysorbate 20

To apply, the user tilts the head sideways and about 3 to 10 drops of the ear formulation is added to the ear using a standard dropper applicator, without having the applicator enter the ear canal. The head is kept tilted for several minutes or the ear is lightly plugged with a wad of cotton to allow the solution to remain in the ear for up to 15 minutes. Then the head is tilted and excess solution is allowed to drain from the ear. Gentle washing with a soft rubber bulb ear syringe containing warm water may be used to remove excess. The probiotic solution can be applied occasionally or daily for up to about five days. A physician should be consulted if there is drainage, discharge, rash, severe irritation in the ear or if the patient experiences dizziness.

Example 12

Prophylactic or Treatment for Athlete's Foot

For prevention or treatment of athlete's foot (tineal fungal infection), the feet are washed with soap and water, dried thoroughly and a powder, cream, lotion, ointment or gel, such as those described in the above examples is applied to the entire foot area. Optimally, the formulation includes about $10^5$ to about $10^8$ *B. coagulans* spores or 0.5% to 20% *B. coagulans* supernatant or filtrate. Daily treatments are continued as needed.

Additionally, athlete's foot may be prevented or treated by using a standard insole insert (e.g. a fabric, fiber or synthetic foam) having sprayed on the surface or impregnated therein with the *B. coagulans* probiotic or extracellular antifungal product. Such treated insoles may be worn daily for up to two to three months when they are replace with fresh treated insoles.

The invention has been described in the above examples using a variety of formulations, although it should be apparent that various other carrier agents that are compatible with the probiotic compositions may be substituted in the examples to give similar results. Accordingly, the invention may be embodied in other specific forms without departing from it in spirit. The examples are to be considered in all respects only as illustrative and not as restrictive, and the scope of the invention is indicated by the claims that follow. All modifications which come within the meaning and range of the lawful equivalency of the claims are to be embraced within their scope.

What is claimed is:

1. A method of inhibiting yeast or fungal infection comprising:
applying topically to skin or a mucous membrane of a mammal a probiotic composition comprising a bacterial component, said bacterial component consisting of *Bacillus coagulans* Hammer (ATCC# 31284); and allowing the *Bacillus coagulans* bacteria to grow topically for sufficient time to inhibit growth of yeast or fungus, thereby inhibiting the yeast or fungal infection.

2. The method of claim 1, wherein said *Bacillus coagulans* bacteria are provided in the form of spores.

3. The method of claim 1 wherein said composition contains $10^3$ to $10^{12}$ viable bacteria or spores per gram of composition.

4. The method of claim 1 wherein said method comprises applying from $10^8$ to $10^{10}$ viable bacteria or spores per day.

5. The method of claim 1 wherein said method comprises applying from $5 \times 10^8$ to $10^9$ viable bacteria or spores per day.

6. The method of claim 1 wherein said composition comprises an effective amount of a fructo-oligosaccharide (FOS).

7. The method of claim 6 wherein said FOS is present in an amount of from about 10 to 1000 milligrams per gram of composition.

8. The method of claim 6 wherein said FOS is present in an amount of from about 100 to 500 milligrams per gram of composition.

9. The method of claim 1, wherein said fungus is selected from the group consisting of *Trichophyton mentagrophytes, Trichophyton interdigitale, Trichophyton rubrum*, and *Trichophyton yaoundei*.

10. The method of claim 1, wherein the applying step comprises applying a probiotic composition in the form of a cream, lotion, gel, oil, ointment, suspension, aerosol spray, powder, aerosol powder or semi-solid formulation.

11. A method of inhibiting growth of yeast or fungus or a combination thereof, comprising: applying a composition comprising a bacterial component consisting of *Bacillus coagulans* Hammer (ATCC# 31284) to a solid surface; contacting the solid surface with the applied *Bacillus coagulans* bacteria thereon to skin or a mucous membrane of a mammal; and allowing the solid surface to contact the skin or mucous membrane for sufficient time to allow initiation of probiotic activity of the *Bacillus coagulans* bacteria to inhibit growth of yeast or fungus or a combination thereof adjacent to or on the skin or mucous membrane.

12. The method of claim 11, wherein the solid surface comprises a flexible article selected from the group consisting of a diaper, pliable material for wiping skin or a mucous membrane, dermal patch, adhesive tape, absorbent pad, tampon and article of clothing.

13. The method of claim 11, wherein the applying step comprises impregnating the composition into a fibrous or nonfibrous solid matrix.

14. The method of claim 11, wherein the bacterial component is included in the composition in the form of spores.

15. The method of claim 11, wherein the bacterial component is included in the composition in the form of a dried cell mass.

16. The method of claim 11 wherein said composition contains $10^3$ to $10^{12}$ viable bacteria or spores per gram of composition.

17. The method of claim 11 wherein said composition comprises an effective amount of a fructo-oligosaccharide (FOS).

18. The method of claim 17 wherein said FOS is present in an amount of from about 10 to 1000 milligrams per gram of composition.

19. The method of claim 17 wherein said FOS is present in an amount of from about 100 to 500 milligrams per gram of composition.

20. A method of treating a vaginal infection, comprising: identifying a subject suffering from a vaginal infection; and applying topically to the skin or a mucous membrane of said subject a composition comprising a bacterial component consisting of *Bacillus coagulans* Hammer (ATCC# 31284).

21. The method of claim 20, wherein said infection is caused by a yeast pathogen.

22. The method of claim 21, wherein said yeast pathogen is selected from the group consisting of *Candida albicans, Candida tropicalis*, and a combination thereof.

23. The method of claim 20, wherein said composition is in a form selected from the group consisting of a douche, bath salt, soap, powdered bubble bath, bath powder, bath oil, cream, liquid, powder, non-soap emollient cleanser, suppository, soft towelette, and aerosol microparticulate.

24. The method of claim 20, wherein the *Bacillus coagulans* bacteria are in the form of spores.

25. The method of claim 20, wherein the *Bacillus coagulans* bacteria are in the form of vegetative cells.

26. The method of claim 20, wherein said composition contains $10^3$ to $10^{12}$ viable bacteria or spores per gram of composition.

27. The method of claim 23, wherein said bath oil further comprises mineral oil, laureth-4, quaternium-18 hectorite and phenylcarbinol.

28. The method of claim 23, wherein said bath oil further comprises olive oil, grape seed oil, emu oil, sweet almond oil, geranium oil, grapefruit oil, mandarin oil or peppermint oil.

29. The method of claim 23, wherein said bath oil further comprises a fragrance.

30. The method of claim 23, wherein said non-soap emollient cleanser further comprises sodium octoxynol-2 ethane sulfonate, petrolatum, octoxynol-3, mineral oil, lanolin oil, cocamide MEA, or imidazolidinyl urea.

31. The method of claim 23, wherein said soft towelette further comprises potassium sorbate and disodium EDTA.

32. The method of claim 23, wherein said soft towelette further comprises DMDM hydantoin, isopropyl myristate, methylparaben, polysorbate 60, propylene glycol, propylparaben or sorbitan stearate.

33. The method of claim 23, wherein said soft towelette is disposable.

34. The method of claim 23, wherein a symptom of said vaginal infection is selected from the group consisting of vaginal itch and discharge.

35. The method of claim 20, wherein said composition is in the form of a vaginal suppository or insert comprising from about $10^6$ to $10^{12}$ viable *Bacillus coagulans* bacteria.

36. The method of claim 35, wherein between one and about three suppositories or inserts are used per day for a consecutive period of time of about three to about seven days.

37. The method of claim 1, wherein said yeast pathogen is selected from the group consisting of *Candida albicans, Candida tropicalis*, and a combination thereof.

38. The method of claim 11, wherein said yeast pathogen is selected from the group consisting of *Candida albicans, Candida tropicalis*, and a combination thereof.

* * * * *